United States Patent

Rebell et al.

[11] Patent Number: 5,300,108
[45] Date of Patent: Apr. 5, 1994

[54] ACTIVE FIXATION LEAD WITH A DUAL-PITCH, FREE SPINNING COMPOUND SCREW

[75] Inventors: Allan K. Rebell, North Miami; Demetrios I. Doumenis, Miami, both of Fla.

[73] Assignee: Telectronics Pacing Systems, Inc., Englewood, Colo.

[21] Appl. No.: 1,126

[22] Filed: Jan. 5, 1993

[51] Int. Cl.⁵ .............................................. A61N 1/05
[52] U.S. Cl. ................................................. 607/127
[58] Field of Search ................................. 607/126, 127

[56] References Cited

U.S. PATENT DOCUMENTS

| | | | |
|---|---|---|---|
| 4,106,512 | 8/1978 | Bisping | 128/418 |
| 4,217,913 | 8/1980 | Dutcher | 128/785 |
| 4,570,642 | 2/1986 | Kane et al. | 128/785 |
| 5,076,285 | 12/1991 | Hess et al. | 128/186 |
| 5,129,404 | 7/1992 | Spehr et al. | 607/127 |
| 5,228,455 | 7/1993 | Barcel | 607/127 |

Primary Examiner—William E. Kamm
Assistant Examiner—Scott M. Getzow
Attorney, Agent, or Firm—Gottlieb, Rackman & Reisman

[57] ABSTRACT

An active fixation lead assembly including a dual-pitch screw mechanism and a free spinning mechanism, which provides an improved capability for firmly engaging a lead tip upon heart tissue while avoiding damage to the tissue due to overtorquing of the lead. The dual-pitch screw mechanism employs an extendable coupling screw, firmly attached to a helical fixation coil. The thread pitch of the extendable coupling screw is greater than the thread pitch of the helical fixation coil so that the coil portion will move through tissue faster per revolution than the coupling screw, thereby embracing the tissue more tightly against the lead and improving the electrical connection between the tissue and the electrode. Generally, the free spinning mechanism allows the fixation coil to rotate freely after the fixation coil has been fully extended. More particularly, the free spinning mechanism facilitates the use of a low level of torque to cause engagement of the coil with heart tissue so that a physician operator can feel the engagement of the heart tissue with the lead despite the large distance between the lead tip and a stylet knob.

16 Claims, 2 Drawing Sheets

FIG. 1

ACTIVE FIXATION LEAD WITH A DUAL-PITCH, FREE SPINNING COMPOUND SCREW

TECHNICAL FIELD

The present invention relates to a lead for carrying signals or stimulation pulses between a cardiac stimulation device and a patient's heart, and, more particularly, to an improved assembly for anchoring an electrode mounted on the lead in a fixed position with respect to the heart.

BACKGROUND OF THE INVENTION

A cardiac stimulation lead generally includes at least one electrode and a flexible insulated conductor for carrying signals and stimulating pulses between each electrode and a cardiac stimulating device. In the case of a cardiac pacemaker lead, an electrode is passed through the cardiovascular system into a heart chamber, where it is positioned to contact the endocardial wall of the heart. One of various types of fixation devices may be employed to secure an electrode in a fixed position with respect to the cardiac tissue to be stimulated. For example, fins or tines are devices which may be used to passively intertwine with trabeculi within the heart to prevent dislodgement of an electrode. Another common lead fixation strategy employs a sharpened helix, comprising either an electrode itself or a helix adjacent to an electrode, which is affixed to the distal end of an endocardial pacing lead. In this case the helix is rotated by some means from the proximal end of the lead in order to screw the helix into the endocardium and permanently affix the electrode within the heart.

An early method of rotating the helix into heart tissue involved either rotation of the entire lead or rotation of a stylet with a screwdriver tip. Later designs employed fixation helixes that were advanced or retracted into the distal end of the pacing lead to permit passage of the lead through the cardiovascular system without snagging tissue. For example, H. J. Bisping in U.S. Pat. No. 4,106,512, entitled "Transvenously Implantable Lead", issued Aug. 15, 1978, describes a lead in which a helix acts as the electrode and is advanced out of the distal end of the lead by rotation of a coiled conductor within the lead body.

Another approach to rotating a fixation helix out of the distal end of a lead into cardiac tissue employs a screwdriver tip stylet to engage a slot within the distal end of the lead, as taught by R. G. Dutcher in U.S. Pat. No. 4,217,913, entitled "Body-Implantable Lead with Protected, Extendable Tissue Securing Means", issued Aug. 19, 1980. In this patent, the helix serves only to attach the lead to the tissue. A separate ring electrode supplies stimulation pulses. Also, in U.S. Pat. No. 4,570,642, entitled "Endocardial Extendable Screw-In Lead" and issued Feb. 18, 1986, L. M. Kane et al. locate a helix on a member which is slidable within the distal end of the pacing lead. The helix is advanced out of the distal end of the pacing lead by means of a cylindrical stylet which pushes a member located within the distal end of the lead, carrying the fixation helix. The fixation helix is screwed into the tissue by rotation of the entire lead.

For either of these latter two fixation approaches, which involve rotating a helix using a screwdriver tip stylet or rotating a coiled conductor within a lead body, the stylet or coiled conductor does not efficiently transfer torque down the body of the pacing lead. Accordingly, the number of turns of the conductor pin or stylet at the proximal end of the lead does not precisely correspond to the number of rotations of the helix at the distal end of the lead. In U.S. Pat. No. 5,076,285, entitled "Screw-in Lead", issued on Dec. 31, 1991, D. N. Hess et al. disclose a fixed helix type pacing lead which provides means for rotationally fixing a stylet located within the lead at both the proximal and the distal ends of the lead. In this case, torque is transmitted down the lead by both the stylet and the coiled conductor within the lead body. This patent also addresses the problem of helix snagging during implantation by provision of a unique helix configuration in which the helix is tapered, and employs a distal, sharpened point which intersects the central axis of the pacing lead.

Active fixation lead assemblies which are known in the prior art present numerous problems and disadvantages. One major problem with prior art lead assemblies is that an implanting physician must position an electrode firmly against heart tissue before fastening the fixation tip in order to achieve a required level of electrical coupling between the electrode and the tissue. Unfortunately, the heart is constantly in motion. Therefore, even when the physician uses an imaging device such as a fluroscope to visualize the relative positions of the lead tip and the heart tissue, the physician still does not know know whether the lead tip is firmly and appropriately positioned. Furthermore, the procedure of holding the electrode firmly in place and simultaneously turning the coil is difficult in practice.

Another major problem with prior art lead assemblies is that even though a physician may have implanted a lead and fully extended its coil, the electrode may still not be firmly engaged with the heart tissue, resulting in a poor electrical contact and leading to a high stimulation threshold. Furthermore, if the distal end of the lead is not firmly pressed into the cardiac tissue, the fixation device will not physically engage firmly with the heart tissue and will not electrically couple firmly with the heart tissue. If the electrical coupling is insufficient and a better connection is required, the physician must fully retract the coil and restart the fixation procedure.

An additional difficulty with prior art lead assemblies arises when the lead is firmly positioned against the heart prior to affixing the tip. As a helical coil active fixation tip is rotated, heart tissue is drawn up to the electrode. Unfortunately, prior art lead assemblies provide little indication of when the heart tissue meets the electrode. After the electrode has pressed against the heart, a physician may easily overtorque the helical fixation coil, further embedding the coil in heart tissue and possibly causing tearing of delicate heart tissue.

The present invention provides an improved active fixation lead assembly that specifically overcomes the aforementioned problems and disadvantages of the prior art lead assemblies and generally provides other advantages.

The foregoing problems and disadvantages are overcome and numerous other advantages are provided by an active fixation lead assembly in accordance with the present invention that includes a dual-pitch screw mechanism and a free spinning mechanism. The dual-pitch screw mechanism employs an extendable coupling screw which is firmly attached to a helical fixation coil. The thread pitch of the extendable coupling screw is different from the thread pitch of the helical fixation coil. Generally, the free spinning mechanism allows the fixation coil to rotate freely after the fixation coil has been fully extended. More particularly, the free spinning mechanism of the present invention requires only a relatively low level of torque to operate so that a physician operator can feel the engagement of heart tissue with the coil at the tip of the lead despite the large distance (on the order of three feet) between the lead tip and the stylet knob.

One object of the present invention is to provide an active fixation lead which does not require a physician to position the electrode firmly against the heart tissue prior to advancing the fixation coil. The active fixation lead of the present invention does not require that the electrode be firmly placed against the heart prior to affixing the coil. The electrode may be placed in the general vicinity of a desired part of the heart and the coil may be rotated to extend the coil from the lead. After the fixation coil is fully extended, it will continue to rotate freely, drawing the heart tissue up snugly against the distal end of the lead assembly.

A second object of the present invention is to provide an active fixation lead which continues to draw heart tissue toward the electrode even after the fixation coil is fully extended. The active fixation lead of the present invention employs a dual-pitch screw in which the thread pitch of a distal coil portion of the screw is greater than the thread pitch of a proximal coupling screw portion so that the distal coil portion will move through tissue faster per revolution than the proximal screw advances relative to the lead, thereby embracing the tissue more tightly against the electrode housing and improving the electrical connection between the tissue and the electrode. Furthermore, the active fixation lead of the present invention includes a free spinning mechanism. After the fixation coil is fully extended, it will continue to rotate freely, drawing the heart tissue up snugly against the distal end of the lead assembly. Thus, the heart tissue is firmly held by a fixation coil, snugly against the distal end of the electrode. An increased intimacy between the heart tissue and the cardiac stimulating and sensing electrodes increases the surface area of the electrode-tissue interface and reduces the microscopic motion between the electrode and the tissue, thereby reducing irritation of the tissue and improving pacing thresholds. The lead is easier to implant because the lead fixation system does not require that the implanting physician maintain pressure on the lead prior to coil extension.

A third object of the present invention is to provide an active fixation lead in which a tactile feed back signal is given to the implanting physician to cease rotation of the helical fixation coil after the heart tissue is snugly drawn against the electrode. The free spinning mechanism of the active fixation lead of the present invention facilitates such signalling. As the helical coil rotates, the heart tissue is drawn up toward the lead assembly. When the heart tissue meets the lead assembly, the tissue exerts an immediate and positive resistance to further rotation of a stylet knob, providing a significant tactical feedback to the physician indicating that further rotation of the stylet knob is unnecessary and might be injurious to heart tissue. Thus, the active fixation lead helps to prevent accidental advancement of the fixation coil due to inadvertent torque being applied to a stylet during advancement.

An additional object of the present invention is to provide rotational force to a helical coil lead tip using a screwdriver tip stylet which more efficiently transfers torque down the body of the pacing lead. The dual-pitch screw of the present invention is provided with a thread pitch on its distal coil portion which is greater than the thread pitch on its proximal screw portion so that the distal coil portion will move through tissue faster per revolution than the proximal screw portion advances relative to the lead, thereby increasing the efficiency of the fixation procedure by embracing the tissue more tightly against the electrode housing and improving the electrical connection between the tissue and the electrode.

A further object of the present invention is to reduce the size of an electrode housing which holds the screw mechanism of an active helical coil fixation lead. Prior art electrode arrangements have employed a machined or molded nut to hold a coupling screw. In the present invention, a small ball bearing replaces the larger nut.

A still further object of the present invention is to provide a seal located between heart tissue and the threaded mechanism. In prior art active fixation leads, the threaded mechanism was exposed to blood.

Further objects and advantages of the invention will become apparent as the following description proceeds.

SUMMARY OF THE INVENTION

Briefly stated, and in accordance with one embodiment of the present invention, an active fixation cardiac lead for implantation into a patient's heart is provided. This lead comprises an elongated flexible lead body, an electrode housing, a dual-pitch screw located in the housing and means for rotating the dual-pitch screw. The lead body includes at least one insulated conductor. The electrode housing is attached at the distal end of the lead body and includes a generally centrally located conduit and at least one electrode, each of which electrodes is electrically coupled to a corresponding insulated conductor within the lead. A dual-pitch screw, positioned within the electrode housing conduit, incorporates a proximal screw portion and a distal coil portion. When engaged by a rotating means, the proximal screw portion is adapted to rotate and move distally within and with respect to the electrode housing when it is rotated in a first direction, causing the distal coil portion to be extended longitudinally out of the electrode housing. When the proximal screw portion is rotated in an opposite second direction, it is adapted to move proximally within and with respect to the electrode housing, causing the distal coil portion to be retracted longitudinally into the electrode housing. The thread pitch of the distal coil portion, which is adapted to engage the patient's heart, is greater than the thread pitch of the proximal screw portion so that the distal coil portion will advance through tissue faster per revolution than it is advanced by the proximal screw portion, thereby causing the engaged heart tissue to be tightly compacted against the end of the electrode housing and improving the electrical connection between the tissue and the electrode. Furthermore, the lead also includes a means for stopping the longitudinal extension of the distal coil portion of the dual-pitch screw, while allowing its continued first direction rotation with respect to the electrode housing, when the longitudinal extension reaches a predetermined limit.

In accordance with a second embodiment of the present invention, an active fixation cardiac lead is provided comprising an elongated flexible lead body having a proximal end and a distal end. The lead body includes an interior cavity, an insulating sheath and at least one conductor mounted within the insulating sheath, all of which extend longitudinally from the proximal to the distal end of the lead. A stylet is adapted to be inserted into the proximal end of the lead body and extended through its interior cavity to rotatably engage with an electrode assembly at the lead body's distal end. The electrode assembly includes an electrode housing having a generally cylindrical shape, and at least one electrode. Each of the electrodes is electrically coupled to a corresponding one of the conductors within the lead body. The electrode housing includes an internal conduit for accommodating a compound screw and a free spinning mechanism which allows the compound screw to rotate freely, even after it reaches its limit of extension. The compound screw includes a threaded proximal coupling screw or portion and a distal fixation coil or portion, and may be engaged by the stylet and rotated in one direction to extend the fixation coil of the compound screw beyond the housing, or rotated in an opposite direction to retract the fixation coil into the housing.

The threaded coupling screw has a stylet receiving head at its proximal end, a zero pitch track immediately distal to the head and a threaded shaft having its threads at a first predetermined pitch and being positioned between the distal end of the coupling screw and the zero pitch track. The coupling screw head is adapted to be engaged and rotated by the stylet to provide for rotation of the compound screw. The fixation coil is firmly attached to the distal end of the threaded coupling screw and extends distally therefrom. The fixation coil has a greater thread pitch than the threaded coupling screw. The difference in thread pitches between the coupling screw and the fixation coil causes the fixation coil to advance through tissue at a greater rate per revolution of the compound screw than the coupling screw advances within the electrode housing.

The free spinning mechanism includes a first ball bearing, a second ball bearing, an aperture and a spring. The first ball bearing is adapted to rotationally engage the threaded coupling screw within the electrode housing. It is positioned within the conduit in a generally fixed location with respect to the electrode housing. With respect to the threaded coupling screw, the first ball bearing is positioned upon the zero pitch track of the coupling screw when the screw is fully extended and, otherwise, is positioned within the thread trough of the coupling screw. The second ball bearing is positioned a generally fixed interval distal to the first ball bearing. The aperture, which is positioned adjacent to the second ball bearing, extends radially from the interior to the exterior of the electrode channel housing. The spring is located at the exterior periphery of the electrode housing adjacent to and coextensive with the aperture, and exerts a force toward the interior of the housing upon the second ball bearing. The second ball bearing is adapted to be forced out of the conduit and into the aperture by an apex or land on the thread of the threaded coupling screw when the screw is rotated to its full extension and the first ball bearing enters the zero pitch track. When the screw is rotated in the opposite direction, the second ball bearing becomes unaligned with the apex on the thread and the spring forces the second ball bearing out of the aperture and into the electrode housing conduit, within the thread trough of the threaded coupling screw, then the first ball bearing engages the thread of the coupling screw. This rotation thus causes the coupling screw to move proximally relative to the electrode housing and causes the fixation coil to withdraw from the heart tissue.

In accordance with a third embodiment of the present invention, an active fixation cardiac lead is provided comprising an elongated flexible lead body, a stylet, and an electrode assembly, which includes at least one electrode and an electrode housing for accommodating a compound screw and a free spinning mechanism. The elements of this third embodiment of the invention are similar or identical to the second embodiment except that the threaded coupling screw and the helical fixation coil are provided with an identical thread pitch.

BRIEF DESCRIPTION OF THE DRAWINGS

The foregoing aspects and other features of the invention are described and explained in the following detailed description, taken in conjunction with the accompanying drawings, wherein.

DETAILED DESCRIPTION OF THE INVENTION

Figure 1:
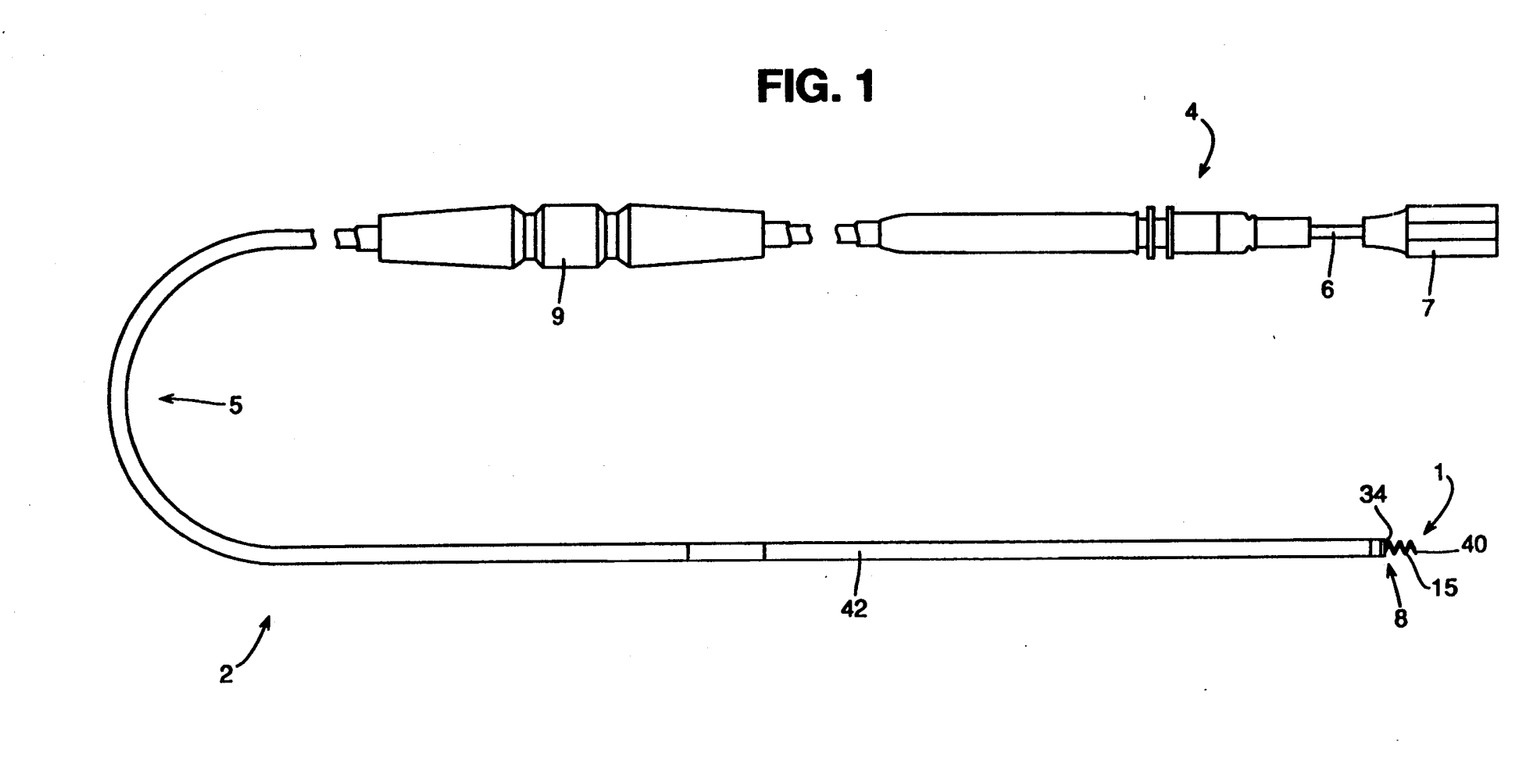
FIG. 1 is a plan view of a cardiac stimulation lead containing the lead fixation system of the present invention.

FIG. 1 is a plan view of a cardiac stimulation lead containing the lead fixation system 1 of the present invention. It illustrates a lead assembly 2 having a generally tubular elongate shape with a proximal portion 4, a midsectional shaft portion 5 and a distal electrode portion 8. An anchoring sleeve 9 forms a boundary between the proximal portion 4 and the midsectional shaft portion 5 of the lead assembly 2 and provides a means for anchoring the lead assembly 2 within the cardiovascular system. Located between the lead assembly proximal portion 4 and the lead assembly distal portion 8, and generally spanning nearly the entire length of the lead assembly 2, is the lead assembly midsectional shaft portion 5 which, referring to FIG. 2 in conjunction with FIG. 1, is generally comprised of a shaft cylinder 42 having a shaft inner channel or lumen 44 enveloped by a flexible, coiled wire conductor 36, a flexible cylindrical inner insulator 46 and a flexible cylindrical shaft outer insulator 48. A stylet 6 (FIG. 1) may be inserted through the shaft inner channel 44 to engage the distal electrode portion 8 of the lead assembly 2 and facilitate its implantation in the patient's heart tissue (not shown) by rotating the stylet knob 7. In general, for various embodiments of the invention, the distal electrode portion 8 of the lead assembly 2 includes at least one electrode 12 for electrically coupling the lead to the patient's heart, and a means for affixing the distal end of the lead to the heart.

Figure 2:
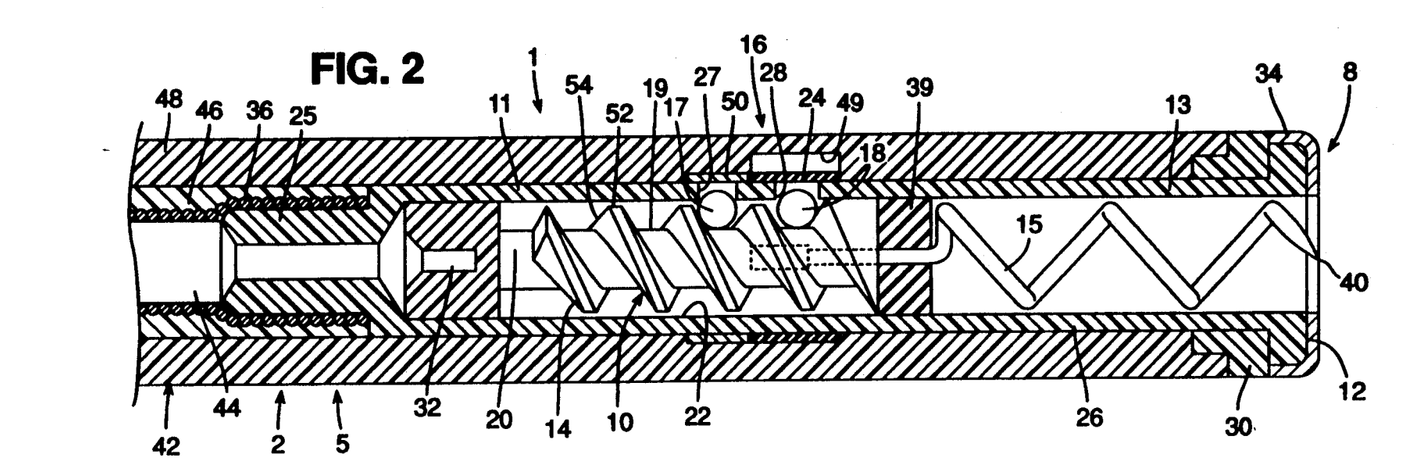
FIG. 2 is a partial cross-sectional view of the distal end of the cardiac stimulation lead of FIG. 1, showing the lead fixation system of the present invention with the helical fixation coil of the compound screw in a retracted position.
Figure 3:
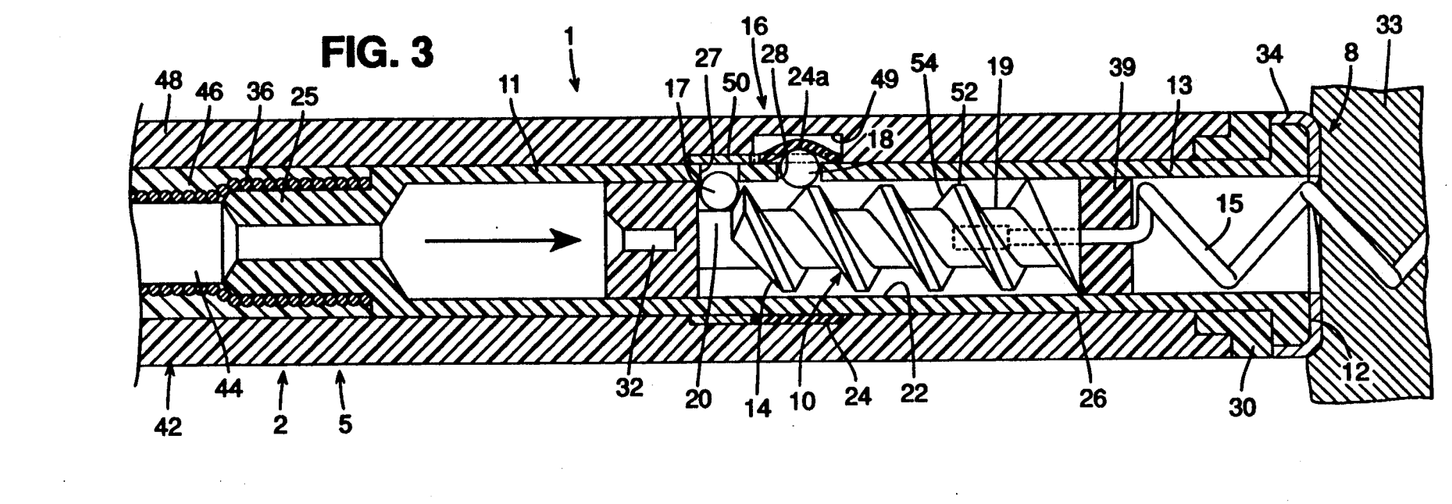
FIG. 3 is a partial cross-sectional view of the distal end of the cardiac stimulation lead shown in FIG. 2 showing the lead fixation system with the helical fixation coil of the compound screw in an extended position.

Referring now to FIG. 2 in particular, the coiled wire conductor 36 is generally tubular in shape and surrounds the shaft inner channel 44. Although the preferred embodiment of the invention is a bipolar lead which includes two conductors and electrodes, only a single conductor/electrode pair 36/12 is illustrated in FIG. 2 and FIG. 3 since a single electrode implementation may be understood with a less complex discussion and since the presence of additional electrodes is not necessary for a full understanding of the invention. Other embodiments of the invention may include a lesser or a greater number of conductor/electrode pairs. The cylindrical inner insulator 46, comprising a dielectric insulating material, fills the space between the conductor 36 and the cylindrical outer insulator 48. The distal end of the coiled wire conductor 36 is electrically and mechanically coupled to the electrode 12. The electrode 12 is comprised of a neck 25 and an electrode cylinder 26. The neck 25 is generally tubular in form and has a reduced inside diameter in comparison to the inside diameter of the electrode cylinder 26 to assist the centering of the tip (not shown) of stylet 6 when the tip is inserted into the lead assembly 2. The electrode neck 25 and cylinder 26 are generally constructed from an electrically conductive material and the cylinder 26 has a tubular shape that includes a proximal end portion 11 and a distal end portion 13. Passing within the electrode cylinder 26 from the proximal end 11 to the distal end 13 is a centrally located electrode cavity 22. Two apertures, a first aperture 27 and a second aperture 28, are bored through the electrode cylinder 26 from its outer diameter into the electrode cavity 22 for reasons which will become further apparent below.

A porous electrode coating or layer 34 is provided to improve the electrically-conducting interface between the electrode 12 and heart tissue 33 (FIG. 3). The porous structure provides a substrate for tissue ingrowth and an augmented surface area to reduce the polarization impedance of the lead, which, in turn, improves its stimulating and sensing capabilities. In the preferred embodiment of the invention, the porous electrode layer 34 is coupled to a steroid-eluting collar 30 which delivers an anti-inflammatory steroid to the stimulation site of the heart tissue to reduce the adverse reaction of the tissue to the stimulation electrode. The cylindrical outer insulator 48 of the lead is constructed from a dielectric insulating material and may be in the form of a cylindrical tube which surrounds the electrode cylinder 26, the distal end of conductor 36 and the cylindrical inner insulator 46.

A cylindrical reciprocating silicon seal 39, positioned between a threaded coupling screw 14 and a helical fixation coil 15 of a compound screw 10 and within the cavity 22 of electrode cylinder 26, serves as a seal to prevent entry of blood and other body fluids into the shaft inner channel 44 and into the threaded coupling screw 14 portion of the electrode cavity 22. This seal, located between the heart tissue 33 and the threaded coupling screw 14, is an improvement over prior art active fixation leads, in which the threaded mechanism was exposed to blood. The reciprocating silicon seal 39 acts as a dynamic seal when the stylet 6 has engaged and is rotating the coupling screw 14, and otherwise acts as a static seal. In addition to its sealing function, the reciprocating silicon seal 39 serves as a support for and assists in centering of the helical fixation screw 15 within the electrode cavity 22.

The lead fixation system 1 employs two structural components which cause the lead 2 to firmly engage biological tissue, the compound screw shown generally at 10 and a free spin assembly, shown generally at 16. The first component, compound screw 10, is axially movable between a "retracted" position, shown in FIG. 2, and an "extended" position, shown in FIG. 3. Screw 10 comprises the threaded coupling screw 14, and, firmly bound to the threaded coupling screw 14, the helical fixation coil 15, the coils of which are provided with a greater pitch than are the threads of the threaded coupling screw 14. The threaded coupling screw 14 is constructed from a cast or molded insulative epoxy material. The helical fixation coil 15 comprises a metal coil which is firmly attached to the threaded coupling screw 14 such that any rotational or axial motion applied to one structure extends to the other structure. In one exemplary embodiment of the invention, the tail or proximal portion of the fixation coil 15 is insert-casted into the coupling screw 14 so as to insulate the fixation coil 15 from the electrode 12. The coarse helical fixation coil 15 is generally comprised of coiled spring metal formed in a cork-screw configuration and having a sharp pointed leading tip 40 for penetrating and boring into a patient's heart muscle.

Compound screw 10 is axially moved between its retracted and extended positions upon corresponding rotation of the screw in one or another direction by the stylet 6 of FIG. 1. This movement is caused by the interaction of the thread of coupling screw 14 with first and second ball bearings 17 and 18, respectively. The ball bearings 17 and 18 engage and bear against the walls of apertures 27 and 28 and the thread of coupling screw 14 to cam the compound screw 10 between its extended and retracted positions when the screw 10 is rotated. The compound screw 10 provides for improved effectiveness in implanting the helical fixation coil 15 into the patient's heart tissue 33, or removing it therefrom, due to a difference in thread pitch between the helical fixation coil 15 and the threaded coupling screw 14. The threaded coupling screw 14, which engages and is advanced by the ball bearings 17 and 18, has a relatively fine threading. The helical fixation coil 15, which is driven by the threaded coupling screw 14 and engages heart tissue, has a coarser threading. The difference in thread pitch between the coupling screw 14 and the helical fixation coil 15 causes the fixation coil 15 to axially penetrate heart tissue faster, per revolution, than the coupling screw 14 axially advances. In addition, this combination of thread pitches provides for the advancement of the fixation coil 15 out of the end of electrode 12 at a slower rate than the rate with which it can screw itself into the heart tissue. This causes the electrode 12 to reach its destination (contact with the heart tissue) before the fixation coil 15 is completely screwed into the heart tissue. Accordingly, when the fixation coil 15 is further advanced to its fully extended position, the electrode 12 presses itself into the heart tissue, creating a better connection between the heart tissue and the electrode 12. This lowers the pacing threshold and decreases the stimulation current or voltage required to pace the heart. Furthermore, the finer threads of the proximal threaded coupling screw 14, in comparison to the coarser threads of the fixation coil 15, provide a smoother transition of torque from the stylet 6 to the fixation coil 15 and improve the implanting physicians sensitivity to tactile feedback from the tissue 33.

When a physician removes the helical fixation coil 15 from the patient's heart tissue 33, the difference in pitch between the helical fixation coil 15 and the threaded coupling screw 14 provides that the helical fixation coil 15 retracts from the heart tissue faster, per revolution, than the coupling screw 14 axially recedes in a manner similar to that which occurs when the coil 15 is advanced into the tissue. Therefore, the helical fixation coil 15 is removed from the patient's tissue 33 in fewer rotations than are necessary to fully retract the helical fixation coil 15 into the electrode cavity 22. Thus, the helical fixation coil 15 is somewhat prevented from carrying tissue into the electrode cavity 22. This reduces the likelihood that the fixation coil 15 will pull tissue 33 into the electrode cavity 22 and the shaft inner channel 44, which could otherwise cause jamming of the threaded coupling screw 14 within the distal electrode portion 8 of the lead assembly 2. Jamming of the threaded mechanism is a problem in prior art active fixation leads.

Assuming the compound screw 10 is in its retracted position, as shown in FIG. 2, and the implanting physician firmly positions the porous layer 34 of electrode 12 against the patient's heart tissue 33 before rotating the stylet knob 7 to affix the helical fixation coil 15 to the heart, upon rotation of the compound screw 10 the helical fixation coil starts to move out of the electrode housing and penetrates the heart tissue before the compound screw 10 reaches its extended position, or mechanical limit of extension. Further turning of the stylet 6 to cause the compound screw to reach its extended position will draw the heart tissue more snugly against the porous layer 34 of electrode 12.

If, however, the physician fails to firmly position the porous layer 34 of electrode 12 against the patient's heart prior to rotating the compound screw 10, the helical fixation coil may only partially engage the heart tissue 33 when the compound screw has been fully extended. Thus, the second structural component of the lead fixation system 1, the "free spin assembly" 16, is provided to secure effective fixation of the lead assembly 2 with the heart tissue under such circumstances. The free spin assembly 16 allows the physician to continue to rotate, or "free spin", the compound screw 10 without extending the leading tip 40 of the helical fixation coil 15 any further from the distal end of the distal electrode portion s of lead assembly 2, thus allowing the lead fixation system 1 to draw tissue snuggly up against the lead assembly. The free spin assembly 16 is designed to allow rotation of the helical fixation coil 15, upon the application of a relatively low level of torque to the stylet knob 7, so that the physician can feel the engagement of heart tissue with the distal end of the lead despite the distance between the helical coil 15 and the stylet knob 7. The free spin assembly 16 comprises the electrode 12, the compound screw 10 including a zero thread pitch track 20 at its proximal end, the first ball bearing 17, the second ball bearing 18, a rigid cylindrical collar 50 and an elastomeric insulation spring 24.

The free spin assembly 16 employs the two ball bearings 17 and 18 to mechanically couple the electrode 12 to the threaded coupling portion 14 of the compound screw 10. During manufacture of the lead assembly 2, the first ball bearing 17 and second ball bearing 18 are inserted through the electrode cylinder 26 into the electrode cavity 22 through the first aperture 27 and the second aperture 28, respectively. The rigid cylindrical collar 50 is then placed over the first aperture 27 to prevent the first ball bearing 17 from leaving the electrode cavity 22, and the elastomeric spring 24 is placed over the second aperture 28 to resiliently bias the second ball bearing 18 toward cavity 22 but allow it to move out of the cavity, into a recess 49 provided in outer insulator 48, when urged in that direction with sufficient force by the thread of coupling screw 14. The rigid cylindrical collar 50 is a band, cage or clamp structure composed of a metal such as platinum or platinumiridium alloy. The ball bearings 17 and 18 are standard spheres, common in devices such as watches, which are composed of gemstones such as sapphire, ruby or corundum. In some embodiments of the present invention, including the preferred embodiment, the epoxy coupling screw 14 and the gemstone ball bearings 17 and 18 provide insulation of the helical fixation coil 15 from the electrode 12. In other embodiments of the invention, the first ball bearing 17, the second ball bearing 18 and the coupling screw may be constructed from an electrically conductive material so that the free spin assembly 16 may electrically couple the electrode 12 to the compound screw 10.

The first ball bearing 17 is positioned proximally upon the lead assembly 2 with respect to the second ball bearing 18, farthest from the leading tip 40 of the fixation coil. The rigid cylindrical collar 50 restrains the first ball bearing 17 in a permanent position within the thread of the threaded coupling screw 14, between the outer surface of the cylindrical electrode 12 and an inner core 19 of the threaded coupling screw 14. The second ball bearing 18 is not similarly restrained by the collar 50.

The second ball bearing 18, positioned along the electrode 12 distally with respect to the first ball bearing 17, is normally placed within the thread of the threaded coupling screw 14, between the elastomeric spring 24 on the outer surface of the cylindrical electrode 12 and the inner core 19 of the threaded coupling screw 14, but may also move radially outwardly of the electrode 12 to clear the thread of the threaded coupling screw 14 and allow the compound screw 10 to freely spin in a manner to be described hereinafter. The first ball bearing 17 and second ball bearing 18 are separated by a fixed distance corresponding to a multiple of the pitch of the thread of the threaded coupling screw 14. Thus, the motion of the first ball bearing 17 is correlated with that of the second ball bearing 18.

The first ball bearing 17 serves as a key to engage the electrode 12 with the threaded coupling screw 14 and also serves as a stop to limit the extension of the compound screw 10 from the electrode. As a physician rotates the stylet knob 7 so that the compound screw 10 rotates in a clockwise direction, as viewed from the proximal end of the lead assembly 2, the compound screw 10 advances distally with respect to first ball bearing 17 from its retracted position, shown in FIG. 2 until, as is illustrated in FIG. 3, the first ball bearing 17 lies within the track 20 of the threaded coupling screw 14, Where the thread pitch is reduced to zero and the screw can advance no farther. At this point, the compound screw 10 has reached its extended position and additional clockwise rotation of the compound screw 10 causes the first ball bearing 17 to continually ride within the track 20 without further advancing the compound screw 10. With the compound screw 10 in its extended position, the physician can "free spin" the compound screw so that the helical fixation coil 15 continues to rotate to pull heart tissue 33 up against the lead assembly 2 but it does not extend further out of electrode 12. While this is taking place, the second ball bearing 18 is cammed radially into recess 49, against the bias of elastomeric spring 24, which is shown in a correspondingly deflected condition at 24a in FIG. 3, for a sufficient distance to allow the apex 52 of the thread of coupling screw 14 to pass underneath it. The ball bearing 18 is cammed radially outwardly over the thread apex 52 by a ramp 54 which forms part of the thread of the coupling screw 14. Conversely, to effect return movement of the compound screw 10 from its extended position to its retracted position, the screw is rotated in a counter-clockwise direction. Accordingly, the second ball bearing 18 is urged by spring 24 toward the core 19 of the coupling screw 14 and into the trough formed by the thread on the screw. This provides sufficient positive engagement between the electrode 12 and the coupling screw 14 to cause the coupling screw 14 to move axially from its extended position toward its retracted position. During the initial part of this movement, the ball bearing 17 exits from the zero thread pitch track 20 and enters the trough formed by the thread of coupling screw 14 to assist ball bearing 18 in causing such axial movement.

The second ball bearing 18 is biased toward the core 19 of coupling screw 14 and is allowed to move in and out of the electrode cavity 22, into the second aperture 28 and the recess 49, because of the resilience of elastomeric insulation spring 24. The spring 24 is in the form of a tube of elastomeric insulation (for example, a silicon rubber outer sleeve) surrounding a portion of the outer surface of the electrode 12, within recess 49, and acting on the periphery of the electrode cylinder 26. In an alternate embodiment of the invention, the spring 24 and the recess 49 may be eliminated by utilizing an outer insulator 48 that is made of an elastomeric material. In this case the outer insulator 48 becomes the spring and it deflects radially outwardly as necessary to allow the second ball bearing 18 to pass over the apex 52 of the thread of the coupling screw 14 during free spinning of the compound screw 10. In either case the second ball bearing 18 is designed to lift up, out of the coupling screw 14 thread, and ride over the apex 52 of the coupling screw 14 thread to allow the compound screw 10 to spin freely.

As indicated earlier, when the fixation coil 15 is fully extended and the threaded coupling screw 14 is further rotated, the heart tissue is drawn up snugly against electrode surface 34 at the distal end of lead assembly 2. When the heart tissue 33 meets the electrode surface 34, the tissue exerts an immediate and positive resistance to further rotation of the stylet knob 7, providing a tactile feedback which is easily sensed by the implanting physician and warns the physician not to overtorque the helical fixation coil 15. Thus, the active fixation lead assembly 2 utilizes the positive engagement of the heart tissue with the electrode surface to achieve precise positioning of the fixation coil 15. Moreover, the engagement of the ball bearings 17 and 18 with the coupling screw 14 of the lead assembly prevents accidental axial advancement of the fixation coil 15 which would otherwise occur in the event an inadvertent axial force were to be applied to the stylet 6 during its rotation by the physician.

The usage of a fixation system employing ball bearings 17 and 18 provides a further advantage of the present invention over prior art helical coil designs, namely a reduction in size. Prior art electrode arrangements use a machine or molded nut to hold the coupling screw. In the present invention, a small ball bearing replaces the larger nut.

From the foregoing discussion, it is apparent that the present invention provides an improved, more easily implantable, active fixation lead having improved capability for firmly engaging a lead tip electrode with heart tissue and for signalling the physician of such engagement in order to avoid damage to the tissue due to overtorquing of the lead.

Although the invention has been described with reference to particular embodiments, it is to be understood that such embodiments are merely illustrative of the application of the principles of the invention. Numerous modifications may be made therein and other arrangements may be devised without departing from the true spirit and scope of the invention.

We claim:

1. An active fixation cardiac lead for implantation into a patient's heart, comprising:
   an elongated flexible lead body having at least one insulated conductor and having a proximal end and a distal end;
   an electrode housing positioned at the distal end of said lead body and having a generally centrally located conduit therein, said housing including at least one electrode electrically coupled to said at least one insulated conductor;
   a dual-pitch rotatable screw positioned within said electrode housing conduit, said screw including a proximal screw portion having a first thread pitch therein and being adapted to move axially with respect to said electrode housing from a retracted position to an extended position when rotated in a first direction, and from said extended position to said retracted position when rotated in an opposite second direction, said screw including a distal coil portion having a second thread pitch greater than said first thread pitch, said distal coil portion being adapted to engage tissue in the patient's heart;
   means for rotating said dual-pitch screw with respect to said electrode housing; and
   a free spinning mechanism coupled to said proximal screw portion and responsive to the arrival of said dual-pitch screw at its extended position for limiting said axial movement of said screw while allowing continued first direction rotation of said dual-pitch screw with respect to said electrode housing, whereby said distal coil portion is adapted to draw heart tissue into firm contact with said electrode at the distal end of said lead with continued rotation of the screw after it has reached its extended position.

2. A lead in accordance with claim 1, wherein said rotating means includes a head member carried at the proximal end of said screw, and wherein said dual-pitch screw further comprises:
   a zero pitch track positioned between said head member and said proximal screw portion of said screw, said zero pitch track being in communication with a trough formed by the thread of said proximal screw portion.

3. A lead in accordance with claim 2, wherein said proximal screw portion comprises a threaded coupling screw, wherein said distal coil portion comprises a fixation coil, and wherein said free spinning mechanism further comprises:
   a first ball bearing positioned within said conduit in a generally fixed location with respect to said electrode housing, said first ball bearing being positioned within the zero pitch track of said threaded coupling screw when said screw is in its extended position and, otherwise, being positioned within said thread trough of said threaded coupling screw, said first ball bearing being adapted to rotationally engage said threaded coupling screw with said electrode housing, an aperture extending through said electrode housing, said aperture being positioned a generally fixed interval distal to said first ball bearing, a second ball bearing, said second ball bearing being adapted to be forced into said aperture by the thread of said threaded coupling screw when the screw is rotated to its extended position and, otherwise, being adapted to be forced into a position within the thread trough of said threaded coupling screw to rotationally engage said threaded coupling screw with said electrode housing, and spring means located generally peripherally of said aperture for biasing said second ball bearing toward the interior of said electrode housing and into said thread trough.

4. A lead in accordance with claim 3, wherein said fixation coil is in the shape of a helix.

5. A lead in accordance with claim 3, wherein said spring means comprises a cylindrical elastomeric insulator that surrounds said electrode housing.

6. A lead in accordance with claim 3, wherein said fixation coil is fixably attached to said threaded coupling screw by means of insert casting.

7. An active fixation cardiac lead, comprising:

an elongated flexible lead body having a proximal end and a distal end, said lead body including an interior cavity adapted to receive a rotatable stylet therein, an insulating sheath and at least one conductor mounted within said insulating sheath, said cavity, insulating sheath and at least one conductor extending longitudinally from said proximal end to said distal end; and an electrode assembly carried at said distal end of said lead body, said electrode assembly comprsing:

a generally cylindrical electrode housing having at least one electrode electrically coupled to said at least one conductor and having a conduit therein, a compound screw having a distal end and a proximal end and being adapted to be rotated by said stylet for extension and retraction with respect to said electrode housing, said screw being positioned within the conduit of said electrode housing and including:

a threaded coupling screw, a head positioned at a proximal end of said coupling screw, a zero pitch track positioned immediately distal to said head, said threaded coupling screw comprising a shaft positioned between said zero pitch track and a distal end of said compound screw, said shaft having a thread of predetermined pitch and a thread trough thereon, said head being adapted for engagement and rotation by said stylet, and a fixation coil fixably attached to said threaded coupling screw and extending distally therefrom, said fixation coil having a thread pitch greater than the thread pitch of said threaded coupling screw, and a free spinning mechanism, said mechanism including:

a first ball bearing positioned within said conduit in a generally fixed location with respect to said electrode housing and positioned within said zero pitch track when the threaded coupling screw is fully extended and, otherwise, positioned within the thread trough of said threaded coupling screw, said first ball bearing being adapted to rotationally engage said threaded coupling screw with said electrode housing, an aperture extending through said electrode housing positioned a generally fixed interval distal to said first ball bearing, a spring member located generally peripheral to said aperture exerting a force to the interior of said electrode housing, and a second ball bearing adapted to be forced into said aperture by said thread when the screw is rotated to full extension and said first ball bearing enters said zero pitch track and, otherwise, adapted to be forced into said conduit and within said thread trough by said spring member to rotationally engage said threaded coupling screw with said electrode housing.

8. A lead in accordance with claim 7, wherein said fixation coil is in the shape of a helix.

9. A lead in accordance with claim 7, wherein said spring member comprises a cylindrical elastomeric insulator that surrounds said electrode housing.

10. A lead in accordance with claim 7, wherein said fixation coil is fixably attached to said threaded coupling screw by means of insert casting.

11. An active fixation cardiac lead, comprising:

an elongated flexible lead body having a proximal end and a distal end, said lead body including an interior cavity adapted to receive a rotatable stylet therein, an insulating sheath and at least one conductor mounted within said insulating sheath, said cavity, insulating sheath and at least one conductor extending longitudinally from said proximal end to said distal end; and an electrode assembly carried at said distal end of said lead body, said electrode assembly comprising:

a generally cylindrical electrode housing having at least one electrode electrically coupled to said at least one conductor and having a conduit therein, a compound screw having a distal end and a proximal end and being adapted to be rotated by said stylet for extension and retraction with respect to said electrode housing, said screw being positioned within the conduit of said electrode housing and including:

a threaded coupling screw having a head adapted to be engaged and rotated by said stylet and being positioned on a proximal end of said screw, a zero pitch track positioned immediately distal to said head, said threaded coupling screw comprising a shaft having a thread of predetermined pitch and a thread trough thereon, said shaft being positioned between said zero pitch track and a distal end of said compound screw, and a fixation coil fixably attached to said threaded coupling screw and extending distally therefrom, said coil having a pitch greater than the predetermined pitch of said thread, and a free spinning mechanism, said mechanism including:

a first ball bearing positioned within said conduit in a generally fixed location with respect to said electrode housing and positioned within said zero pitch track when the threaded coupling screw is fully extended and, otherwise, positioned within the thread trough of said threaded coupling screw, said first ball bearing being adapted to rotationally engage said threaded coupling screw with said electrode housing, an aperture extending through said electrode housing positioned a generally fixed interval distal to said first ball bearing, a spring member located generally peripheral to said aperture exerting a force to the interior of said electrode housing, and a second ball bearing adapted to be forced into said aperture by said thread when the screw is rotated to full extension and said first ball bearing enters said zero pitch track and, otherwise, adapted to be forced into said conduit and within said thread trough by said spring member to rotationally engage said threaded coupling screw with said electrode housing.

12. A lead in accordance with claim 11, wherein said fixation coil is in the shape of a helix.

13. A lead in accordance with claim 11, wherein said spring member comprises a cylindrical elastomeric insulator that surrounds said electrode housing.

14. A lead in accordance with claim 11, wherein said fixation coil is fixably attached to said threaded coupling screw by means of insert casting.

15. A method for attaching a cardiac lead to tissue in a patient's heart, said lead including a distal electrode, a compound screw rotatably mounted relative to said electrode for limited axial movement with respect thereto between a retracted position and an extended position when rotated in one or another corresponding directions, said screw including a proximal threaded shaft portion and a distal fixation coil portion, said lead further including a free spinning mechanism permitting said compound screw to continue to be rotated after said screw has been advanced to its extended position, said method including the steps of:

positioning the distal electrode of the lead adjacent to a selected portion of the patient's heart;

rotating the compound screw to axially move the screw toward its extended position and concurrently cause the coil portion thereof to move into engagement with the patient's heart tissue;

continuing rotation of the screw to axially move the screw into its extended position and to more fully engage the coil portion of the screw with the patient's heart tissue;

further continuing rotation of the screw while the screw remains at its extended position to draw the patient's heart tissue fully onto the coil portion of the screw and into engagement with the electrode, whereby a tactile sensation is generated upon engagement of the tissue with the electrode; and terminating the rotation of the screw when the tactile sensation in generated.

16. A method in accordance with claim 15, wherein the thread of said threaded shaft portion of the screw is provided with a predetermined pitch, wherein said fixation coil comprises a helical coil having a pitch that is greater than the pitch of said thread, and wherein the first continuing rotation step includes the sub-step of moving the coil portion axially into the heart tissue at a greater axial rate than the rate at which the screw moves axially relative to the electrode.

* * * * *